(12) United States Patent
Van Der Laken et al.

(10) Patent No.: US 6,831,157 B2
(45) Date of Patent: Dec. 14, 2004

(54) PROCESS FOR THE PURIFICATION OF SERUM ALBUMIN

(75) Inventors: Cornelis Jacobus Van Der Laken, Leiden (NL); Marcellinus Petrus Johannes Piët, Haarlem (NL)

(73) Assignee: DSM IP Assets B.V., Heerlen (NL)

( * ) Notice: Subject to any disclaimer, the term of this patent is extended or adjusted under 35 U.S.C. 154(b) by 148 days.

(21) Appl. No.: 10/334,395

(22) Filed: Dec. 30, 2002

(65) Prior Publication Data

US 2003/0204060 A1 Oct. 30, 2003

Related U.S. Application Data

(62) Division of application No. 09/680,507, filed on Oct. 5, 2000, now Pat. No. 6,504,011, which is a continuation of application No. 08/810,813, filed on Mar. 6, 1997, now Pat. No. 6,150,504, which is a division of application No. 08/352,426, filed on Dec. 8, 1994, now Pat. No. 5,849,874, which is a continuation of application No. 08/286,406, filed on Aug. 5, 1994, now abandoned, which is a continuation of application No. 08/030,214, filed on Mar. 10, 1993, now abandoned.

(51) Int. Cl.[7] .................. C07K 1/00; C07K 14/00; C07K 17/00; C07K 16/00
(52) U.S. Cl. ....................... 530/363; 424/530
(58) Field of Search ............... 530/363; 424/530

(56) References Cited

U.S. PATENT DOCUMENTS

| 4,086,222 A | 4/1978 | Lindquist et al. |
| 4,180,672 A | 12/1979 | Kurozumi et al. |
| 4,228,154 A | 10/1980 | Fisher et al. |
| 5,250,662 A | 10/1993 | Chang |
| 5,250,663 A | 10/1993 | Tenold |
| 6,150,504 A | 11/2000 | Van Der Laken et al. |

FOREIGN PATENT DOCUMENTS

| CA | 1038292 | 9/1978 |
| EP | 0073646 | 3/1983 |
| EP | 0319067 | 6/1989 |
| EP | 0361991 | 4/1990 |
| EP | 0422769 | 4/1991 |
| EP | 0428758 | 5/1991 |
| EP | 0452753 | 10/1991 |
| JP | 4-234326 | 8/1992 |

OTHER PUBLICATIONS

Harris et al., Protein Purification Methods (1989) pp. 245–246.
Kragh–Hansen, Pharmacol. Rev. (1981) 33:17–53.
Scouten, Affinity Chromatography (1981) p. 48–49.
Stoltz et al., Bio–Sciences (1987) 6(4):103–106.
Peters, Adv. Prot. Chem. (1985) 37:161–245.
White et al., Principles of Biochemistry, (1978) p. 581.
Wichman et al., Biochim. Biophys. Acta. (1974) 372:218–224.
Wilchek et al., Methods in Enzymology (1984) 104:3.
Yang and Tsao, Ad. Biochem. Engin. (1982) 25:1942.

Primary Examiner—James Ketter
Assistant Examiner—Konstantina Katcheves
(74) Attorney, Agent, or Firm—Morrison & Foerster LLP

(57) ABSTRACT

Recombinantly produced serum albumin is purified in a series of steps, optionally by incubation with an anion-exchange adsorbent, followed by affinity chromatography employing a hydrophobic solid phase and using a water-soluble lipid anion as desorbens in the aqueous phase. Said immobile phase comprises a carrier coupled to a 2-mercapto or 2-hydroxy alkanoic acid.

5 Claims, 6 Drawing Sheets ered by anion-exchange chromatography and finally affinity chromatography yields a product with a good yield and purity. In EP-A-0319067 a BrCN-activated Sepharose 4B support was mentioned which was prepared
PROCESS FOR THE PURIFICATION OF SERUM ALBUMIN

CROSS-REFERENCE TO RELATED APPLICATIONS

This application is a divisional application of U.S. Ser. No. 09/680,507 filed 5 Oct. 2000 now U.S. Pat. No. 6,504, 011 and now allowed which is a continuation of U.S. Ser. No. 08/810,813 filed 6 March 1997, now U.S. Pat No. 6,150,504; which is a divisional of U.S. Ser. No. 08/352,426 filed 8 Dec. 1994, now U.S. Pat. No. 5,849,874 which is a continuation of U.S. Ser. No. 08/286,406 filed 5 Aug. 1994 and now abandoned which is a continuation of U.S. Ser. No. 08/030,214 filed 10 Mar. 1993 and now abandoned; which application is the national phase of PCT application NL 92/00125 filed 10 Jul. 1992 which, in turn, claims priority from European application 91/201861.1 filed 12 Jul. 1991. The contents of these applications are incorporated herein by reference.

INTRODUCTION TECHNICAL FIELD

The field concerns purification of serum albumins, particularly human serum albumins.

BACKGROUND AND RELEVANT LITERATURE

Human serum albumin (HSA) is the major protein component of plasma. The primary function of albumin in plasma is maintenance of the colloid osmotic pressure within the blood vessel. Furthermore, the protein acts as a carrier of several ligands, for instance bilirubin and fatty acids. (See reviews by F. Rothstein, V. M. Rosenoer and W. L. Hughes in *Albumin Struct. Funct. Uses* (1977) 7–25; U. Kragh-Hansen, *Pharmacol. Rev.* (1981) 33: 17–53; T. Peters Jr., *Adv. Prot. Chem.* (1985) 37: 161–245).

Purified serum albumin is indicated for the prevention and treatment of hypovolemic shock, in conditions where there is severe hypoalbuminemia, as an adjunct in haemodialysis and in cardiopulmonary bypass procedures and in conjunction with exchange transfusion in the treatment of neonatal hyperbilirubinemia.

Since large amounts of serum albumin are necessary for therapy and the source of serum albumin (plasma) is limited, other techniques have been sought to produce HSA in large quantities. Successes have been reported in the production of HSA by fermentation using transformed microorganisms or cell lines made by recombinant DNA techniques. See, for example, EP-A-0073646.

However, one of the major problems in the purification of serum albumin produced by fermentation using transformed cells is the presence of contaminating components from the growth medium (fermentation broth) or cell lysate, which have to be removed in order to obtain purified, homogeneous serum albumin.

In EP-A-0361991 the purification of HSA produced with transformed yeast, using techniques known in the art, yields a product of more than 99% purity. For a pharmaceutical preparation a higher purity is desirable.

Recently a process for the purification of serum albumins based on a process in three steps was disclosed in EP-A-0319067. This process starting with an alkaline precipitation step followed by anion-exchange chromatography and finally affinity chromatography yields a product with a good yield and purity. In EP-A-0319067 a BrCN-activated Sepharose 4B support was mentioned which was prepared according to the method described by Wichman and Andersson (1974). For industrial use the affinity matrix based on BrCN-activated sepharose has two major drawbacks.

First, the isourea linkage (M. Wilchek, T. Miron and J. Kohn in: *Methods in Enzymology* (1984) 104:3, W. B. Jakoley Ed., Academic Press, London) resulting from the reaction with the primary alkylamine (spacer) has a positive charge under physiological conditions. This charged spacer shows anion-exchange like characteristics that might interfere with the biospecific adsorption. A second disadvantage is the limited stability of the isourea linkage under slightly alkaline conditions (C. M. Yang and G. T. Tsao in: *Ad. Biochem. Engin.* (1982) 25:19, A. Fiechter Ed., Springer Verlag, Berlin-Heidelberg) which enables the use of this matrix under sanitizing conditions (0.1–2.0 M NaOH) necessary for the production of pharmaceutical products.

Therefore, there is a great need for a practical process for large-scale purification of human serum albumin with a high recovery and a very high purity.

SUMMARY OF THE INVENTION

Human serum albumin, produced by a transformed host, is purified by ion-exchange chromatography, followed by affinity chromatography employing a lipophilic surface immobile phase comprising a carrier coupled to a 2-mercapto or 2-hydroxy C4–C14 alkanoic acid, or salt or ester thereof. The serum albumin degradation products present at the end of the fermentation which strongly resemble the mature, intact albumin are selectively removed by the fatty acid affinity chromatography applied. High recovery and extremely high purity are achieved.

DESCRIPTION OF THE SPECIFIC EMBODIMENTS

Figure 1:
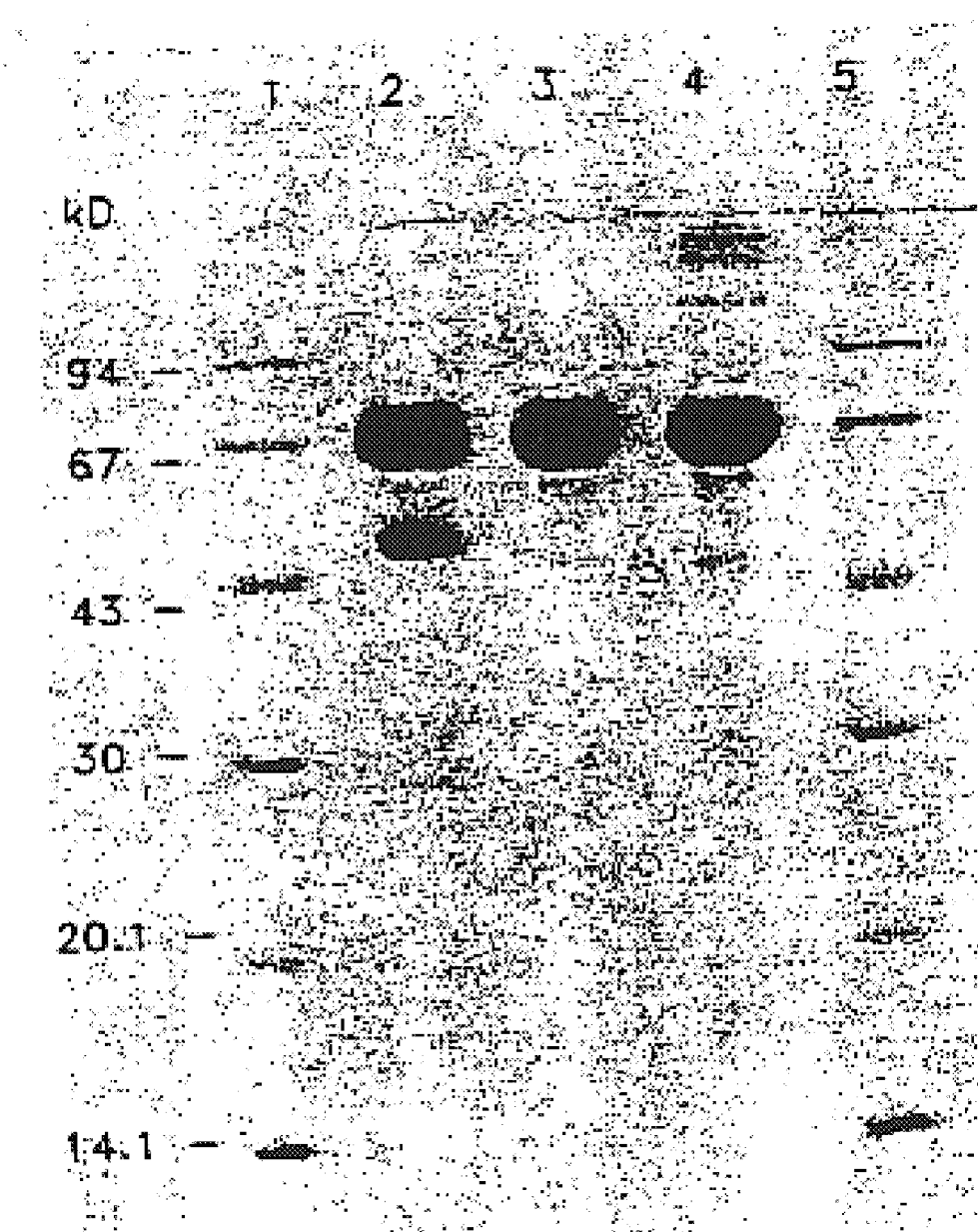
FIG. 1: SDS-PAGE under reducing conditions (CBB R-250 stain). Molecular weight markers: lanes 1 and 5 (24 µg). Purified recombinant HSA after Q-sepharose and affinity chromatography: lane 3 (30 µg). Commercially available from human blood derived HSA (Sigma human albumin No. A-8763: lot: 109F-9304): lane 4 (30 µg).

In accordance with the subject invention, human serum albumin, prepared by fermentation using transformed hosts, e.g. microorganisms or cell lines, made by recombinant DNA techniques, is purified with high recovery and in high purity for use as a pharmacological product. The purification method is preceded by centrifugation and ultrafiltration of a fermentation broth. The method can be applied to the thus obtained supernatant or to the cells after lysis. It generally involves the following steps:

binding of the serum albumin under slightly acidic conditions to an anion-exchange resin; the albumin is desorbed from the resin by lowering the pH of the eluens;

next, optionally, ultrafiltration of the medium;

finally, the essential chromatographic step consisting of affinity chromatography employing a lipophilic immobile phase composed of a hydrophilic matrix, spacer and fatty acid derivative as ligand and a lipophilic anion as desorbens in the eluens.

The serum albumin may then be harvested by desalting and concentration. The serum albumin produced by the subject process is substantially homogeneous and monomeric, viz. more than 99.95% pure.

The method finds use with the production of serum albumin, particularly human serum albumin, prepared by recombinant techniques employing microorganisms or cell lines. The microorganisms may be prokaryotic or eukaryotic, particularly eukaryotic, and include bacteria such as *E. coli, B. subtilis, B. licheniformis, Streptomyces, Pseudomonas*, etc.

Among eukaryotes are yeasts, such as *Saccharomyces, Schizosaccharomyces, Kluvveromyces, Candida*, etc., filamentous fungi, *Neurospora, Aspergillus*, etc.

The expression of the serum albumin may result in secretion or retention of the product in the organism. The broth may be removed batch-wise or continuously from the fermenter. In the case of secretion, the cell-free supernatant is used in the purification process. The cell-free supernatant is obtained by clarification of the fermentation broth, conveniently by centrifuging and/or filtering the broth, using ultrafiltration for concentration of the protein product. The filter will generally have a cut-off of 500–100,000 D, more usually at least about 10,000 D.

Where the product or part thereof is retained in the cytoplasm of the cell, the cells are harvested. A lysate may be produced in accordance with any convenient technique, using mechanical or chemical disruption of the cells to produce the lysate. The cellular debris may be removed by centrifugation.

The pH of the cell-free supernatant or cell lysate is adjusted to about 5 to 9, more preferably to about 6 to 6.5. The pH may be modified by any convenient means, such as the addition of sodium hydroxide, or other convenient base, usually at a normality in the range of about 0.1 to concentrated.

The next step is anion-exchange chromatography. The cell-free supernatant with a buffer concentration from about 20 to 200 mM will be applied to the preconditioned column. The loading of the anion gel will be from 5 to 50 g of protein per liter gel, more preferably from 15 to 25 g of protein per liter gel.

Next the gel can be washed with equilibration buffer. The volume of the washes is not critical, generally being from 0.5–10 based on the volume of the gel. The buffer will generally have a conductivity of 0.1–100 mS/cm, preferably between about 1 to 10 mS/cm. The albumin is desorbed from the gel by eluting with a generally dilute buffer of moderately low pH. The buffer concentration will be from 10 to 100 mM. Desirably the buffer will be at a pH in the range of about pH 4.0–6.0, more desirable between pH 4.25 and 4.75.

The ion-exchange step removes nucleic acids, endotoxins and the major part of the contaminating non-albumin like proteins. Anion-exchange Adsorbents such as QAE or DEAE bound to a commercially available carrier are employed.

The next essential step is affinity chromatography, where a lipophilic immobile phase is used. The binding of the lipophilic molecules to the gel is performed by using a bifunctional reagent, capable of both activating and coupling of the lipophilic molecules. Examples of such reagent are epoxy compounds, as for instance epihalohydrin, such as epichlorohydrin, or bisoxirans such as an alkanediolether, for instance 1,4-butane-dioldiglycidoxyether. The reaction with the gel matrix yields derivatives which possess a hydrophilic, reactive epoxide which can react with nucleophilic ligands such as 2-mercapto or 2-hydroxy C4–C14 alkanoic acids. See for more details: *Affinity Chromatography: A Practical Approach*, ed. Dean, P. D. G., Johnson, W. S. and Middle, F. A., IRL Press, Oxford, England, ISBN-0-904147-71-1.

These affinity chromatographic adsorbents are highly stable and do not possess a charge in the spacer.

After the ion-exchange step the pH of the medium must be increased to physiologic conditions, normally in the range of about 6.5 to 8.0, more usually in the range of about 7 to 7.5. The buffer concentration will generally be in the range of 50 to 250 mM. After applying the medium to the column the gel is washed with equilibration buffer. The volume of the washes is not critical, generally being from 0.25–5 volume based on the volume of the gel. The buffer will generally have a conductivity of 1.0–20 mS/cm, preferably between about 10 to 15 mS/cm. The loading of the affinity gel will be from 5–70 g of protein per liter gel, more preferably from 15–30 g of protein per liter gel. The albumin is eluted by applying a buffer with a fatty acid with a concentration of 25–250 mM, for instance sodium caprylate.

Besides mature human serum albumin, specific degradation products are present in the supernatant of the fermentation broth. These degradation products have a molecular weight of 40–50 kD and consist of domain I and II of the mature protein that comprises three domains. Domain III absent in said 40–50 kD fragment contains the principle fatty acid binding site of albumin (T. Peters, supra). Surprisingly, said 40–50 kD fragments show a higher affinity for lipophilic affinity matrix than mature human serum albumin which enables the separation of the 40–50 kD fragments from the mature protein.

A wide variety of supports and adsorbents may be used as the solid carriers or supports. Such solid carriers include inorganic carriers, such as glass and silica gel, organic, synthetic or naturally occurring carriers, such as, for instance, agarose, cellulose, dextran, polyamide, polyacrylamides, vinyl copolymers of bifunctional acrylates, and various hydroxylated monomers, and the like. Commercially available carriers are sold under the names of Sephadex®, Sepharose®, Trisacryl®, Ultrogel®, Dynospheres®, Macrosorb®, XAD resins, and others.

The conditions for the various steps will be carried out at non-denaturing conditions, generally at convenient temperatures in the range of about −10° C. to +30° C., more usually at about ambient temperatures. The chromatographic steps may be performed batch-wise or continuously, as convenient. Any convenient method of separation may be employed, such as centrifugation, filtration, decanting, or the like. In this way a preparation of isolated serum albumin with a surprisingly high purity of more than 99.9% pure, particularly more than 99.95% pure, can be obtained.

All documents cited are incorporated herein by reference.

The following non-limitative examples will further illustrate the invention.

EXAMPLES

Example 1

Synthesis of Affinity Matrices

E-C10-C10:

E stands for epoxy-activated sepharose 6FF;

first C10 stands for the spacer length of 10 C atoms;

second C10 stands for the number of C atoms in the carboxylic acid ligand.

For the synthesis of the affinity matrices well known methods were used (see e.g. Dean et al., supra).

For the preparation of C3 and C10 spacers epichlorohydrin and 1,4 butanediolglycidoxyether were used, respectively.

Synthesis of the E-C10-C10 Matrix:

1 l Sepharose 6FF was washed thoroughly with distilled water. The excess water was removed by a sintered glass filter. The gel was suspended in 0.6 l of 1,4 butanediolglycidoxyether and stirred for approximately 30 min. Next 0.6 l of a solution of 0.5 N NaOH was added and stirring was continued for 24 h. The epoxy-activated gel was thoroughly washed with distilled water and stored at 0° C. Yield 0.7 kg of wet product (E-C10).

The epoxy-activated sepharose 6FF (0.5 kg of wet product, E-C10) was suspended in a solution of 8 g 2-mercaptodecanoic acid in a solution of 0.5 M sodium carbonate and stirred for 24 h. The gel was filtered on a sintered glass filter and washed successively with 0.2 M sodium carbonate and water. The wet gel was stored at 0° C. This matrix was called E-C10-C10.

The number of free carboxylic acids was determined by simple titration and was found to be 19.3 µequivalents per gram of wet gel matrix.

Example 2

Purification of Recombinant HSA from a Clarified Fermentation Broth by Q-Sepharose and E-C10-C10-Affinity Chromatography Fermentation:

The *Kluvveromyces lactis* strain CBS 2360 (Centraal Bureau voor Schimmelcultures, Baarn, The Netherlands), transformed with a plasmid containing the gene for HSA, was grown for 90 h at 30° C. in a medium containing yeast extract 0.5% (w/v), glucose 1.4% (w/v), casein hydrolysate 1.0% (w/v), vitamins and mineral salts. During the fermentation glucose was fed.

Filtration and Ultrafiltration:

The fermentation broth was centrifuged (5 min at 4000 rpm). The supernatant was filtered through an EKS filter and was concentrated 11 times by ultrafiltration using a filter with a cut-off of 30,000 D. The protein concentration after ultrafiltration was 28 mg/ml, of which 65% is monomeric and mature recombinant HSA. The pH was adjusted to 6.4 by addition of 0.5 M sodium acetate pH 5.5.

Q-Sepharose Chromatography:

The HSA solution was bound to a Q-sepharose FF column (load: 25 g of protein per liter sepharose), which has been equilibrated with 50 mM sodium acetate pH 5.5. After washing the gel with the equilibration buffer, the RHA was eluted with 50 mM sodium acetate pH 4.6. The pH of the eluate was increased to pH 7.4 by addition of 1 M phosphate buffer pH 6.6 (ratio eluate:buffer (v/v)=10:1) and 4 M NaOH. The protein concentration was 10 mg/ml, of which 78% is monomeric and mature recombinant HSA.

Affinity Chromatography:

The HSA containing Q-sepharose eluate was contacted with 2-mercaptodecanoic acid coupled to epoxy-activated sepharose 6FF by a diglycidylether (E-C10-C10-sepharose) as described in Example 1. The affinity absorbent was equilibrated with 100 mM sodium phosphate buffer pH 7.4. After binding the recombinant HSA to the absorbent (load: 22 g of protein per liter gel) the column was washed with the equilibration buffer. The HSA was eluted with 100 mM sodium phosphate pH 7.4 containing 75 mM sodium caprylate. The HSA was desalted and concentrated by ultrafiltration using a filter with a cut-off of 30,000 D. The purified HSA had a protein concentration of 55 mg/ml, of which more than 99.9% was monomeric and mature HSA.

Figure 2:
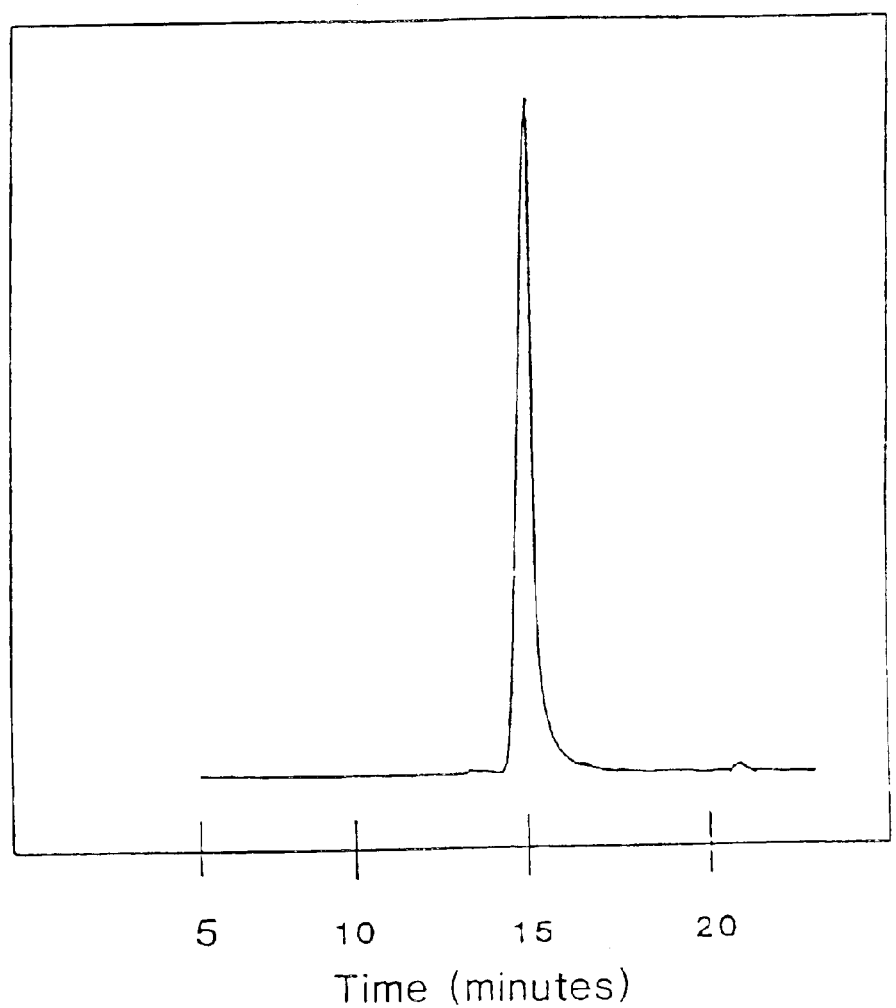
FIG. 2: High performance size-exclusion chromatography on Biosil TSK-250® of purified recombinant HSA.
Figure 3:
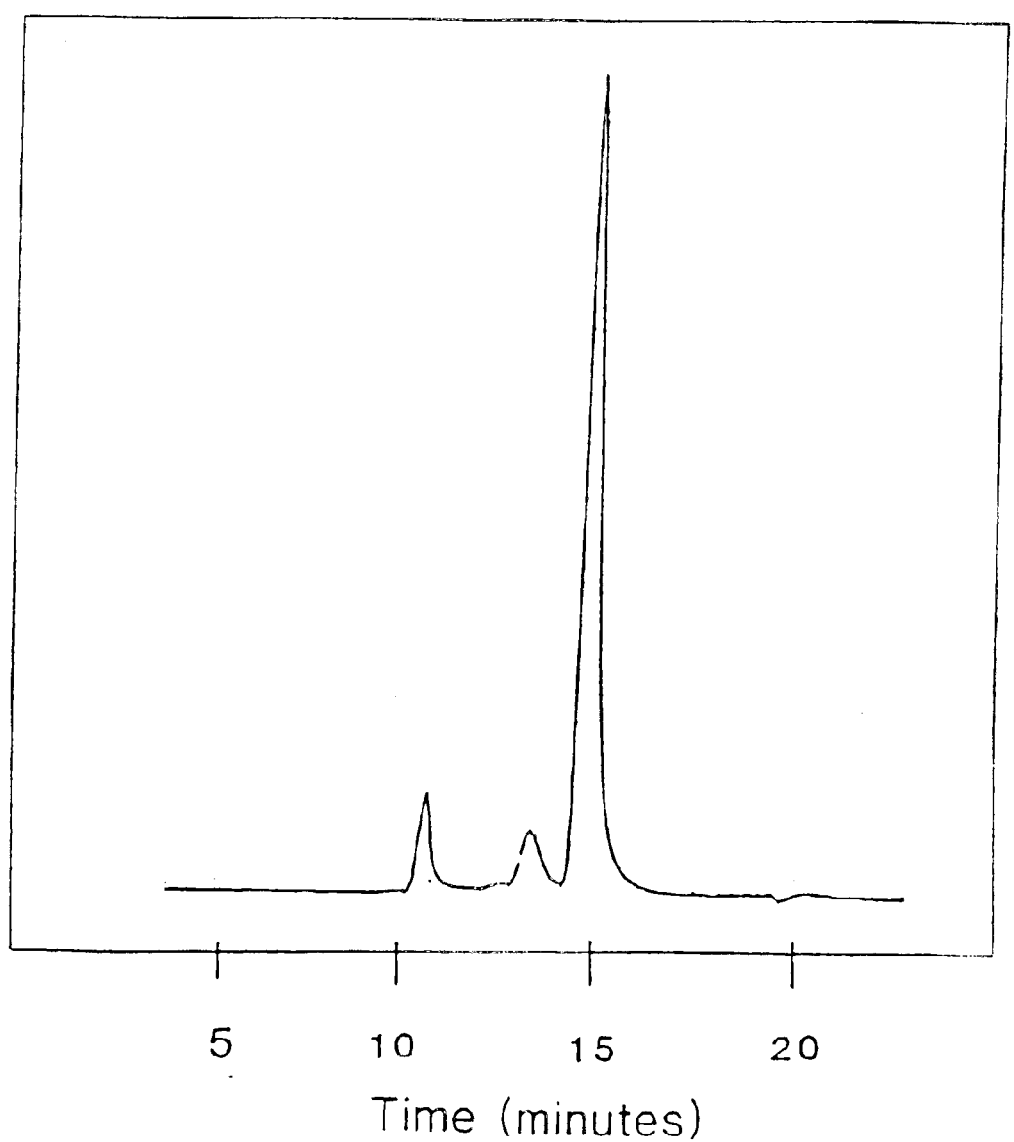
FIG. 3: High performance size-exclusion chromatography on Biosil TSK-250® of commercially available from human blood derived HSA.
Figure 4:
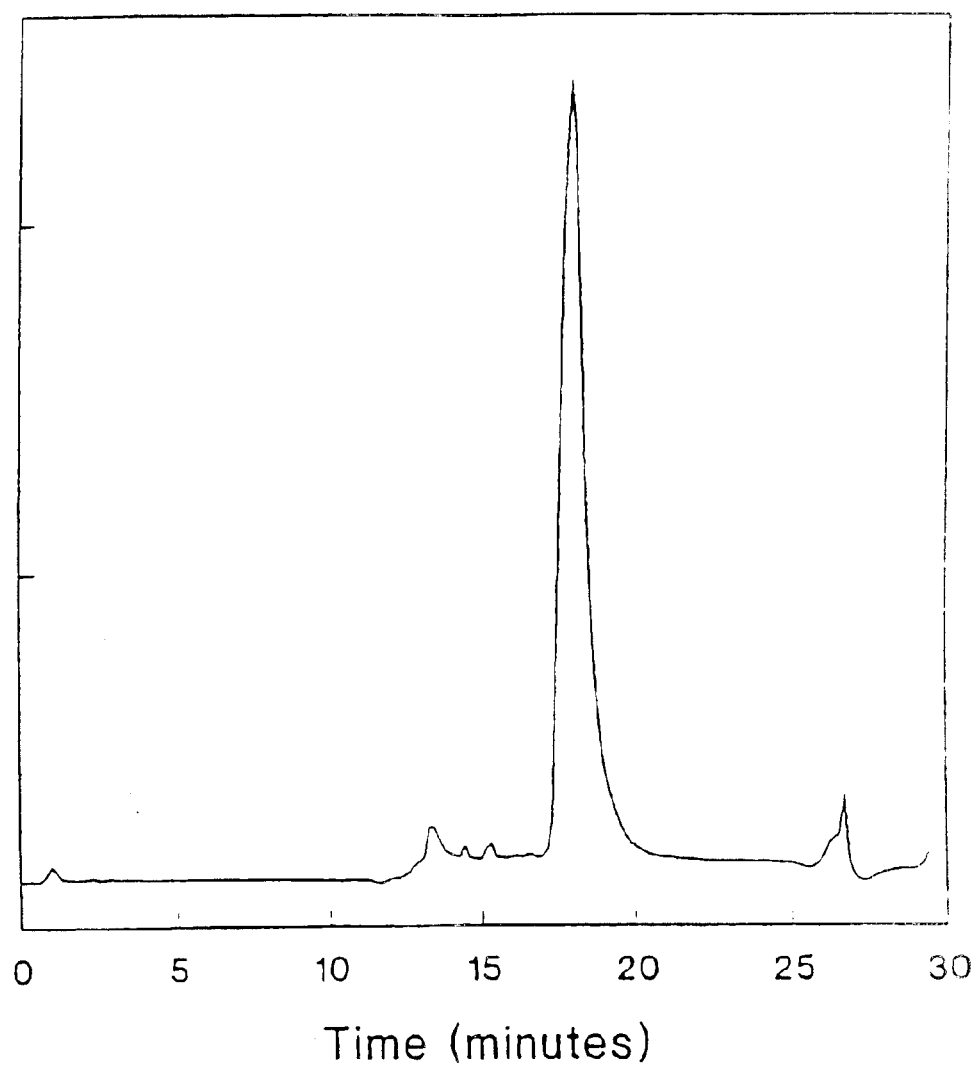
FIG. 4: High performance ion-exchange chromatography on Mono Q® of purified recombinant HSA after Q-sepharose and affinity chromatography.
Figure 5:
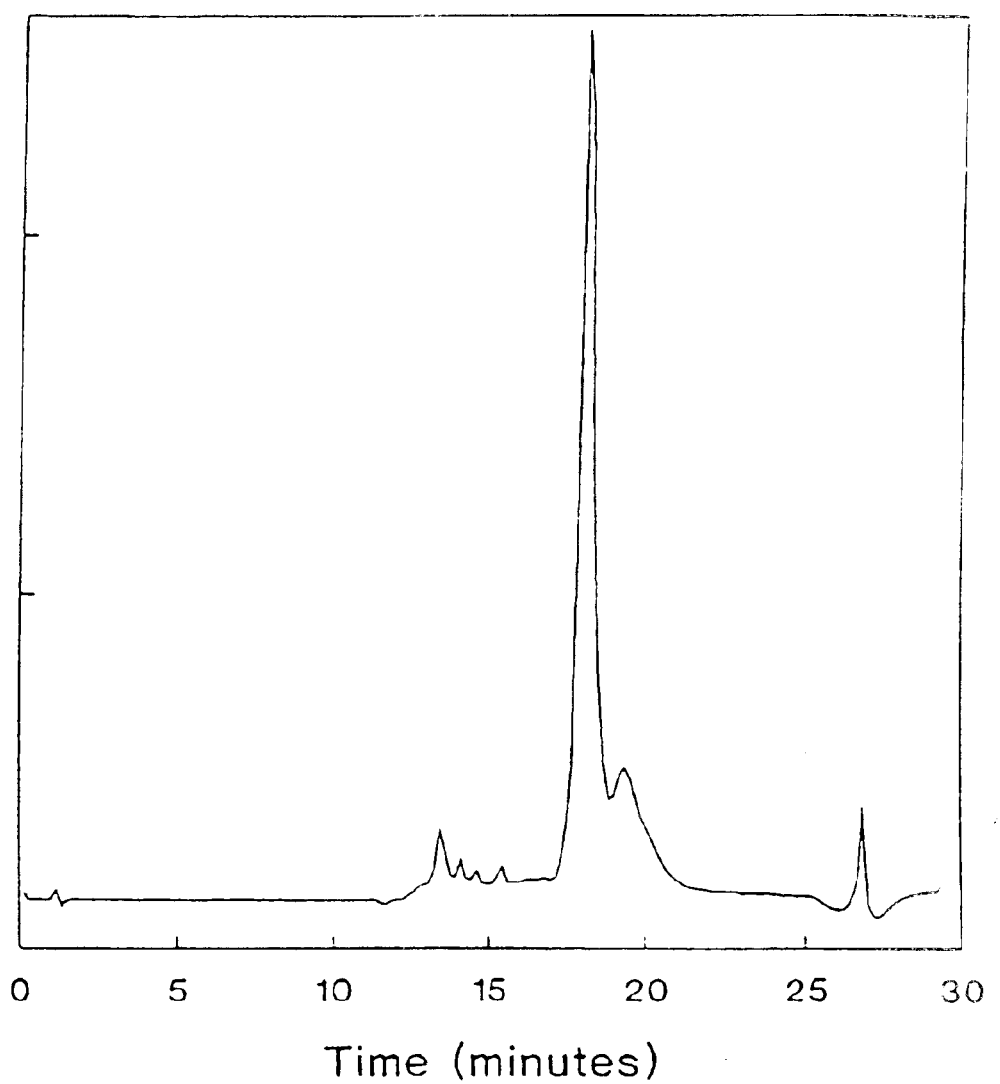
FIG. 5: High performance ion-exchange chromatography on Mono Q® of commercially available from human blood derived HSA after Q-sepharose and affinity chromatography.
Figure 6:
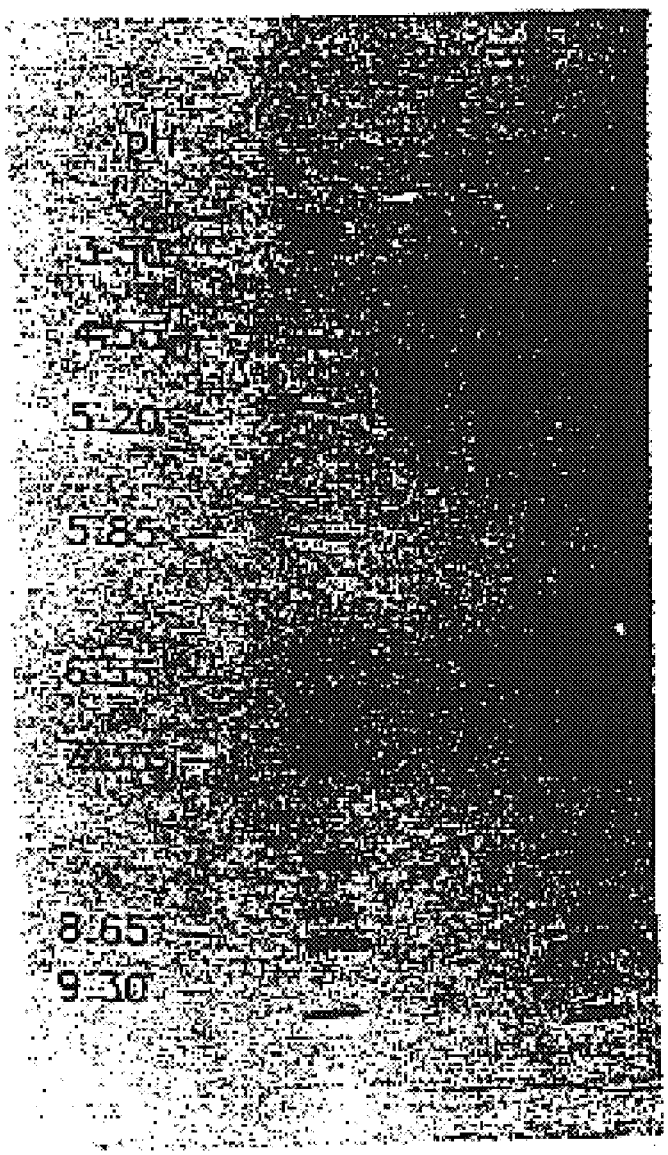
FIG. 6: Isoelectrofocussing (CBB R-250 stain). Markers (lanes 1 and 4), purified recombinant HSA after Q-sepharose and affinity chromatography (lane 2 (20 µg)) and commercially available from human blood derived HSA (lane 3 (20 µg)).

In this example the recovery of HSA was 50%. No contaminants and only trace amounts of degradation products could be detected by SDS-PAGE (FIG. 1), HPLC-SEC (FIGS. 2+3), HPLC-IEC (FIGS. 4+5) and IEF (FIG. 6). The purity according to HPLC-SEC was found to be 99.3%. Correction for the salt related peak at 24.77 gives a purity of >99.91%. In fact, using immunoblotting techniques the purity of the purified HSA was estimated to be at least 99.95%. For this technique polyclonal antibodies were raised against proteins, which were purified from a blank *K. lactis* fermentation broth according to the method described in this example. The level of endotoxin was lower than 1 endotoxin unit per ml 5% (w/v) recombinant HSA concentrate. Endotoxin units are related to the reference standard (RSE) delivered by the FDA, the so-called EC-5. Endotoxin was mainly removed during the Q-sepharose column step, see Table 1.

TABLE 1 removal of endotoxin during purification of recombinant human serum albumin

| Composition | Total endotoxin units |
|---|---|
| *K. lactis* supernatant | 115,000 |
| effluent Q-sepharose | 113,000 |
| eluate Q-sepharose | 59 |
| effluent affinity-matrix | 41 |
| eluate affinity-matrix | 41 |
| end product (5.5% (w/v) HSA) | 17 |

Example 3A

Purification of Recombinant HSA from a Clarified Fermentation Broth by Q-Sepharose and E-C10-C8-Affinity Chromatography Fermentation, filtration and ultrafiltration: performed as described in Example 2.

Q-sepharose chromatography: performed as described in EP-A-0319067.

The collected supernatants were concentrated by ultrafiltration using a filter with a cut-off of 30,000 D. The pH of the retentate was adjusted to pH 7.4. The concentration of monomeric HSA was 14 mg/ml.

Affinity Chromatography with E-C10-C8-Matrix:

The concentrated Q-sepharose eluate was added to C8 (2-mercaptooctanoic acid) coupled to epoxy-activated sepharose 6FF by a diglycidylether. The affinity absorbent was equilibrated and washed after absorption with 100 mM sodium phosphate buffer 7.4. The monomeric HSA and degradation products could be eluated by 100 mM sodium caprylate. Intact HSA and degradation products could be separated by using a gradient of 0–100 mM sodium caprylate in 100 mM sodium phosphate buffer pH 7.4. Binding of HSA and degradation products to the E-C10-C8-matrix was less strong than binding to the E-C10-C10-matrix as described in Example 2.

Example 3B

Purification of Recombinant HSA from a Clarified Fermentation Broth by Q-Sepharose and E-C3-C12-Affinity Chromatography Fermentation, filtration, ultrafiltration and Q-sepharose chromatography: performed as described in Example 3A.

Affinity chromatography with E-C3-C12-matrix:

The purification of HSA was performed as described in Example 3A, except 2-mercaptododecaoctanoic acid was coupled to epoxy-activated sepharose 6FF by C3-ether. Bound monomeric and mature HSA, degradation products of HSA and other contaminations could not be eluted by 100 mM sodium caprylate in 100 mM sodium phosphate buffer pH 7.4. However, elution was possible with 1% SDS. Separation of intact HSA and other proteins was not possible.

What is claimed is:

1. A method to treat hypoalbuminemia which method comprises administering to a subject in need of such treatment an effective amount of a composition of isolated monomeric human serum albumin, more than 99.9% pure, wherein the composition is free of 40–50 Kd serum albumin fragments having domains 1 and 2 of mature serum abumin.

2. The method of claim 1, wherein said composition further contains a pharmaceutically acceptable excipient.

3. The method of claim 1, wherein the isolated monomeric human serum albumin is more than 99.95% pure.

4. The method of claim 3, wherein said composition further contains a pharmaceutically acceptable excipient.

5. The method of claim 1, wherein said composition contains said human serum albumin at a concentration of at least 55 mg/ml.

* * * * *

UNITED STATES PATENT AND TRADEMARK OFFICE
CERTIFICATE OF CORRECTION

| | | |
|---|---|---|
| PATENT NO. | : 6,831,157 B2 | Page 1 of 1 |
| APPLICATION NO. | : 10/334395 | |
| DATED | : December 14, 2004 | |
| INVENTOR(S) | : Van Der Laken et al. | |

It is certified that error appears in the above-identified patent and that said Letters Patent is hereby corrected as shown below:

Title page, Item (62), Related U.S. Application Data, insert immediately before the end of the sentence: --, which is a national phase of application No. PCT/NL92/00125, filed on Jul. 10, 1992, now abandoned--.

Title page, Item (30), Foreign Application Priority Data, insert on a separate line under the heading:
--Jul. 12, 1991        (EP) . . . . . . . . . . . . . . . 91201861--.

Signed and Sealed this

Twenty-second Day of May, 2007

JON W. DUDAS
*Director of the United States Patent and Trademark Office*